United States Patent
Supiez (10) Patent No.: US 8,475,364 B2
(45) Date of Patent: Jul. 2, 2013

(54) ENDOTRACHEAL INTUBATION SYSTEM AND INTUBATION PROCEDURE

(76) Inventor: Frederic Supiez, Vienne (FR)

( * ) Notice: Subject to any disclaimer, the term of this patent is extended or adjusted under 35 U.S.C. 154(b) by 740 days.

(21) Appl. No.: 12/667,565

(22) PCT Filed: Jul. 2, 2008

(86) PCT No.: PCT/IB2008/002483
§ 371 (c)(1),
(2), (4) Date: Jan. 13, 2010

(87) PCT Pub. No.: WO2009/004483
PCT Pub. Date: Jan. 8, 2009

(65) Prior Publication Data
US 2010/0191054 A1    Jul. 29, 2010

Related U.S. Application Data

(60) Provisional application No. 60/929,540, filed on Jul. 2, 2007.

(51) Int. Cl.
*A61B 1/00* (2006.01)
*A61B 1/04* (2006.01)
*A61B 1/267* (2006.01)

(52) U.S. Cl.
USPC ............ 600/120; 600/109; 600/118; 600/194

(58) Field of Classification Search
USPC ................. 600/120, 122, 109, 160, 101, 104, 600/106, 116
See application file for complete search history.

(56) References Cited

U.S. PATENT DOCUMENTS

| 4,589,410 | A | | 5/1986 | Miller |
| 5,285,778 | A | | 2/1994 | Mackin |
| 5,327,881 | A | * | 7/1994 | Greene .................. 600/120 |
| 2002/0096177 | A1 | | 7/2002 | Toti |
| 2005/0177024 | A1 | | 8/2005 | Mackin |

FOREIGN PATENT DOCUMENTS

| DE | 20116532 U1 | 2/2002 |
| EP | 1177809 A1 | 2/2002 |
| GB | 2160773 | 1/1986 |
| WO | 02056951 A1 | 7/2002 |

OTHER PUBLICATIONS

International Search Report PCT/IB2008/002483 Dated Feb. 10, 2009.

* cited by examiner

*Primary Examiner* — Rochelle-Ann J Blackman
(74) *Attorney, Agent, or Firm* — Cantor Colburn LLP (57) ABSTRACT

An endotracheal intubation device includes an inflatable cuff connected to an inflation tube, visualization means, where the visualization means include means to enlighten and an image guide, where the means to enlighten, the image guide, and the inflation tube are associated to a first three ways connector adapted to connect the endotracheal intubation device to a control panel; a packaging is also provided containing the endotracheal intubation device wherein the first three ways connector is placed across the packaging so as to allow checking the endotracheal intubation device without impairing its sterility with an endotracheal intubation device tester; an intubation method is further provided using the packaging, the control panel and the endotracheal intubation device tester.

19 Claims, 7 Drawing Sheets

ENDOTRACHEAL INTUBATION SYSTEM AND INTUBATION PROCEDURE

TECHNICAL FIELD

The present invention relates to an endotracheal intubation device adapted for the control of upper aerial ways in reanimation or anesthesia. The present invention further relates to an assembly comprising an endotracheal intubation device and to a procedure using it.

In the present application, the distal end of a component or of a device is to be understood as meaning the end furthest from the practitioner's hand during proper use and the proximal end is to be understood as meaning the end closest to the practitioner's hand during proper use.

BACKGROUND

An intubation is a medical act that should be done by one person under emergency conditions without neither special heavy equipment nor special room. A tube is inserted into a patient's trachea in order to ensure that the airway is not closed and that air is able to reach the lungs. Although endotracheal intubation is regarded as the most reliable available method for protecting a patient's airway, many so called difficult intubations happen leading sometimes to extremely severe consequences including neurological disorders due to hypoxia and to patient's death. The majority of difficult intubations will be predicted by clinical assessment and have been classified into four grades proposed by Dr Cormack, according to the view from the throat. The more the airway appears to be hindered, the highest is the grade and thus the predictable difficulty to intubate. A grade I intubation will proceed straightforward as the trachea is well open and relatively straight whereas a curved or hindered trachea shape present in a grade III or IV intubation (a difficult intubation) will imply repeated attempts at intubation and difficulties or impossibility to introduce the endotracheal tube. These difficulties are due to the low visibility of the airway and are due to the shape the intubation device must adopt.

Many solutions were explored and implemented. An intubation stylet to be inserted into an endotracheal tube is known from EP 1 177 809. Such a stylet is provided with fiber optics and with manipulation means cooperating with a spring which helps bend the tube to a desired form. This kind of stylet can theoretically be used with any kind of endotracheal tube but is costly and non disposable, and multiuse. It therefore does not meet decontamination requirements.

The patent document WO 02/056951 describes a tracheal tube comprising a light guide and an aspiration trocar allowing visualization of the airway of the patient during intubation and suctioning the debris. The patent document U.S. 5,285,778 describes an endotracheal tube comprising a pair of optical fibers to enlighten and to visualize the area around the distal end of the endotracheal tube during the intubation. None of the existing solutions permit to solve in a satisfying manner the problems encountered during difficult intubations. In particular a stylet as described in EP 1 177 809 is required, which represent a source of possible contamination.

Any intubation procedure implies that the cuff of the endotracheal intubation device must be carefully controlled prior to intubation in order to ensure the patient's throat will be hermetically closed to potential gastric reflux. Moreover the sterility of the device prior to and all through the intubation must be preserved which complicate significantly the control procedure.

Prior to a surgery an endotracheal intubation device must be controlled and prepared to counter possible complications. Opening of the sterile packaging is generally required to control the cuff and the endotracheal intubation device must be thus disposed of, no matter the endotracheal intubation device has been used during the surgery.

In emergency case, controlling the cuff means a loss of time that should be reduced.

There is a need for an endotracheal intubation device that allows simplified procedures and that avoids all the above mentioned issues. There is still a need also of an endotracheal intubation device facilitating so called difficult intubation without any help of an external device like a stylet. The present invention is designed to overcome at least part of the aforementioned difficulties or drawbacks and to help conduct the intubation into the trachea without any external device.

BRIEF SUMMARY

The present invention describes an endotracheal intubation device including a main tube having a peripheral wall, a proximal end portion, a central portion and a distal end portion and comprising, an inflatable cuff being disposed on the main tube in sealed relation thereto adjacent to the distal end portion and connected to an inflation tube and visualization means characterized in that said visualization means comprise means to enlighten the area around the distal end portion towards the intubation direction, and in that an image guide extends from the distal end portion to at least the proximal end portion.

In an embodiment of the present invention, said means to enlighten, said image guide, and said inflation tube are associated to a first three ways connector adapted to connect said endotracheal intubation device to a control panel. The three ways connector permits to minimize the time lost during the control procedure or optimize the manner said endotracheal intubation device is carried out. An endotracheal intubation device according to the present invention affords a visualization of the trachea during intubation and the controlling means help the practitioner to direct the distal extremity of the endotracheal intubation device through the meandering or hindered trachea.

In an embodiment of the present invention, an endotracheal intubation device further comprises controlling means for directing the distal end portion, said controlling means comprising proximal prehension means linked to bending means, and said bending means being integrally mounted in the peripheral wall in the central portion of said main tube in a way to permit bend the main tube. Said controlling means facilitate the introduction of the andotracheal intubation device without the help of any external device. An endotracheal intubation device according to the present invention affords a visualization of the trachea during intubation and the controlling means help the practitioner to direct the distal extremity of the endotracheal intubation device through the meandering or hindered trachea.

In an embodiment of the present invention, said bending means comprise at least one transversal groove made on said peripheral wall and a plurality of pulling lines, each pulling line being adapted to bring the edges of a transversal groove closer. The position where a transversal groove is made on said peripheral wall defines a bowing zone. Each transversal groove brings flexibility to said main tube and define an expected bending place. Preferably, each transversal groove extends half along the periphery of said peripheral wall so as to define a prefered bending direction.

In an embodiment of the present invention, a plurality of transversal grooves are realized at some distance from each other. Preferably, two transversal groove are realized on the peripheral wall symetrically in respect to the longitudinal axe and at some distance from each other. Such a configuration lets the practitioner easily obtain an "S"-shaped bending.

In an embodiment of the present invention, each transversal groove can be covered with a thin and elastic protection patch.

In an embodiment of the present invention, said prehension means comprise two manipulation rings. The endotracheal intubation according to the present invention permit the practitioner to bend the main tube using only two fingers of one hand while the other hand is busy holding a laryngoscope required by the usual intubation procedure.

In an embodiment of the present invention, each said pulling line slides inside a longitudinal channel incorporated into the peripheral wall and extends to at least the distal edge of a transversal groove, and the distal end of the pulling line is blocked towards the proximal direction by locking means so that said pulling line constantly straddles said transversal groove.

An endotracheal intubation device according to the present invention is cheap and can be made disposable. An endotracheal intubation device according to the present invention is intended for single-use and allow sterilization before being packaged.

The present invention further relates to a packaging containing an endotracheal intubation device provided with said first three ways connector according to the present invention, characterized in that said packaging is adapted to seal and maintain said endotracheal intubation device in sterile conditions and wherein said first three ways connector extends outside said packaging. Said packaging allows the endotracheal intubation device included in the packaging to be verified without impairing its sterility.

In an embodiment of the present invention, a packaging according to the present invention further comprises a tube having a non expandable diameter of the order of that of a trachea, said tube being inserted onto the cuff of said endotracheal intubation device.

In an embodiment of the present invention, a packaging further has a test pattern placed inside it so as to face the distal end of said endotracheal intubation device placed therein, said test pattern allowing to check visualizing means of said endotracheal intubation device.

The present invention relates also to an endotracheal intubation device tester comprising a case adapted to receive a packaging according to the present invention, a cover to close said case, a pressure controller, an optical or video device, a test light source and a second three way connector connectable to said first three ways connector of the endotracheal intubation device, said inflation tube and said pressure controller being connectable together through a first way of said first and second three ways connectors, said test light source and said means to enlighten being connectable together through a second way of said first and second three ways connectors, and said optical or video device and said image guide being connectable together through a third way of said first and second three ways connectors.

In an embodiment of the present invention, the endotracheal intubation device tester comprises a printer delivering a sticker. Said sticker can collect the test results.

The endotracheal intubation device tester of the present invention allows to check all technical features of the endotracheal intubation device.

The present invention relates as well to an intubation assembly comprising an endotracheal intubation device provided with a first three ways connector according to the present invention and a control panel characterized in that said control panel comprise a pressure regulator, imaging means, a light source, and a third three ways connector, said inflation tube and said pressure regulator being connectable together through a first way of said first and third three ways connectors, said light source and said means to enlighten being connectable together through a second way of said first and third three ways connectors, said image guide and said imaging means being connectable together through a third way of said first and third three ways connectors.

Alternatively, an intubation assembly according to the present invention comprises a packaging according to the present invention and a control panel, said control panel comprising a pressure regulator, imaging means, a light source, and a third three ways connector, said inflation tube and said pressure regulator being connectable together through a first way of said first and third three ways connectors, said light source and said means to enlighten being connectable together through a second way of said first and third three ways connectors, said image guide and said imaging means being connectable together through a third way of said first and third three ways connectors.

In an embodiment of the present invention, said imaging means comprise an image sensor adapted to transmit a video signal to a display device.

Said control panel included in the intubation assembly, once connected to said endotracheal in tubation device through said first and third three ways connectors, controls the pressure into the cuff and permits to the practitioner to vizualize the patient's trachea all through the intubation.

In an embodiment of the present invention, at least said imaging means are mounted on a laryngoscope.

In an embodiment of the present invention, an intubation assembly according to the present invention further comprises an endotracheal intubation device tester according to the present invention.

Finally, the present invention relates to an intubation method using an intubation assembly provided with a three ways connector according to the present invention and comprising a preliminary step of testing said endotracheal intubation device with the help of an endotracheal intubation device tester without impairing the sterility of said packaging.

BRIEF DESCRIPTION OF THE DRAWINGS

The present invention will now be further described in reference to the following description and attached drawings in which.

Referring now to the drawings, the present invention will now be described in detail.

DETAILED DESCRIPTION

Figure 1:
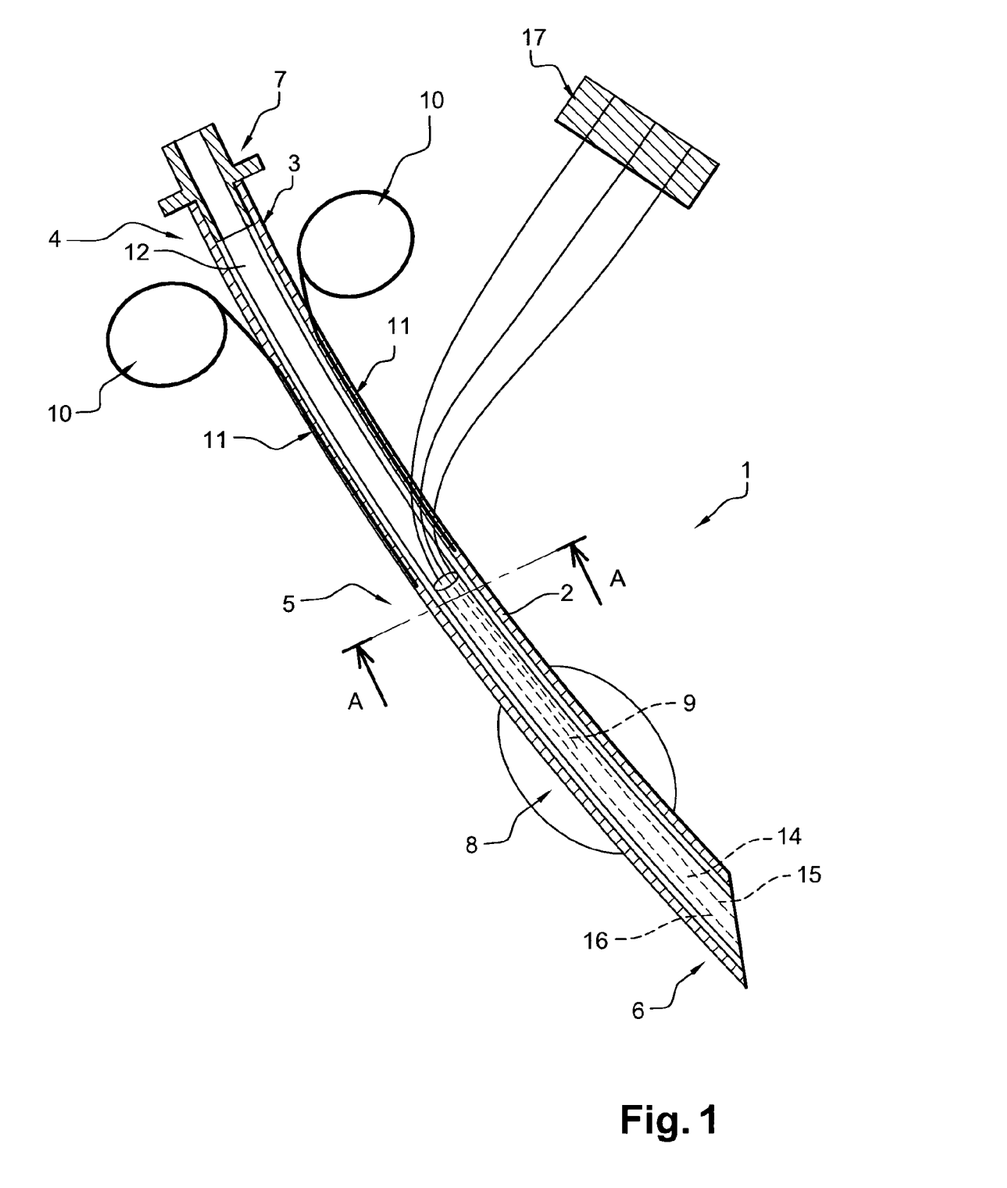
FIG. 1 is a section view of an endotracheal intubation device according to the invention.

FIG. 1 shows a section view of an endotracheal intubation device 1 according to the invention. The endotracheal intubation device 1 comprises a main tube 2 having a peripheral wall 3, a proximal end portion 4, a central portion 5 and a distal end portion 6. The proximal end of said main tube 2 is provided with an adaptor 7. The endotracheal intubation device 1 comprises also a cuff 8 inflatable and disposed on the main tube 2 in sealed relation thereto adjacent to the distal end portion 6. The cuff 8 is connected to an inflation tube 9. The main tube 2 is also provided with controlling means including two manipulation rings 10 and pulling lines 11 extending from said manipulation rings 10. The peripheral wall 3 delineates a main channel 12 adapted for the air passage extending from the proximal end portion 4 to the distal end portion 6.

Figures 2, 3:
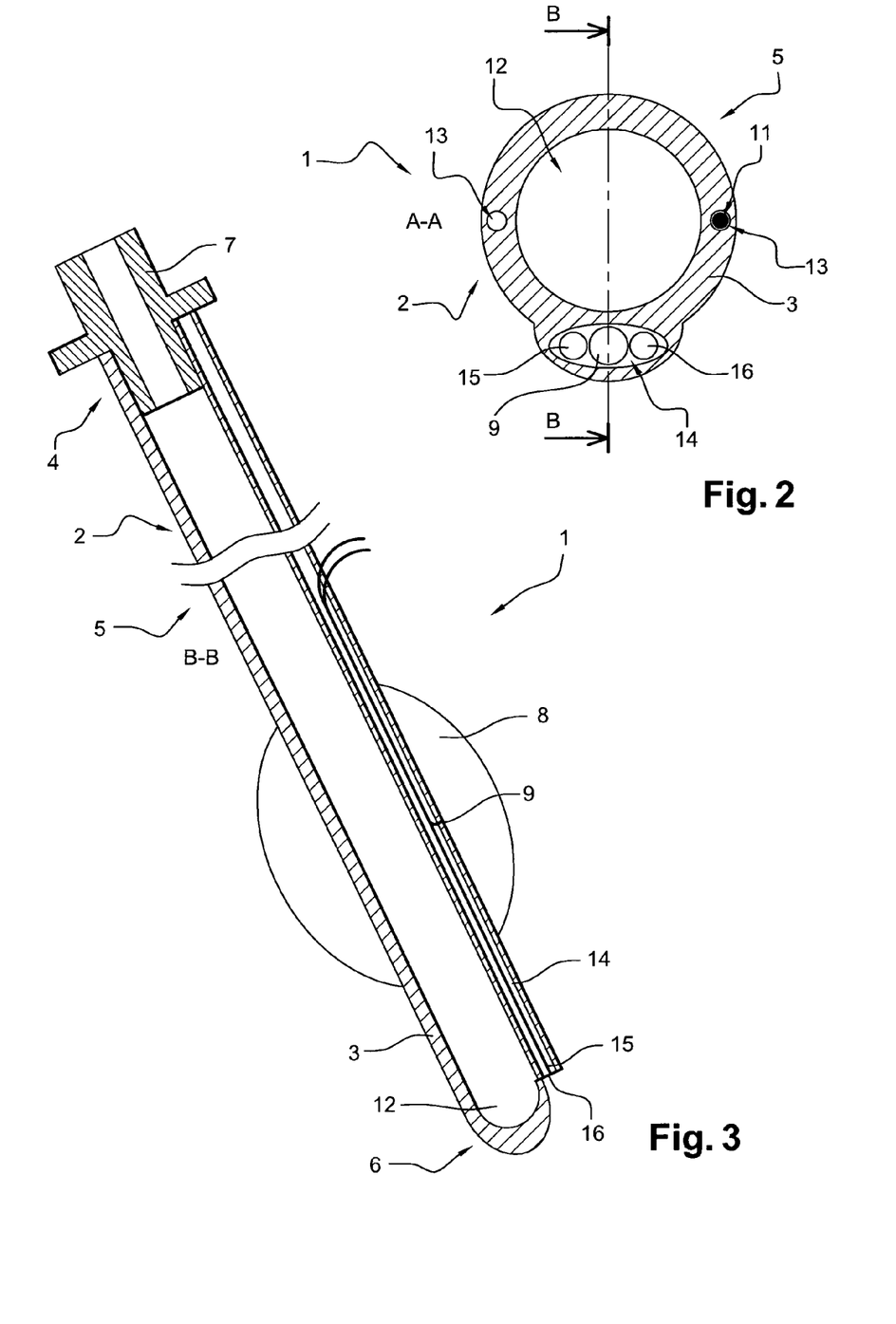
FIG. 2 is a transversal cross section view according to A-A shown on FIG. 1.
FIG. 3 is a longitudinal cross section view according to B-B shown on FIG. 2.

As shown on FIG. 2 and FIG. 3, each pulling line 11 is guided inside a longitudinal guiding channel 13 incorporated into the peripheral wall 3, each pulling line 11 extending to different distance from the proximal end of said main tube 2. A longitudinal second channel 14 extends from at least the central portion 5 of the main wall 2 to the distal end portion 6 of the main tube 2. Inside said second channel 14 are guided the inflation tube 1, means to enlighten composed of a light guide 15 and an image guide 16. The inflation tube 9 exits said second channel 14 into the inflatable cuff 8 whereas said light guide 15 and image guide 16 exit the second channel 14 at the distal end of the main tube 2. The light guide 15 conducts light from a light source to the distal end of said main tube 2 so as to enlighten the area in front of the endotracheal intubation device 1 towards the intubation direction.

Said inflation tube 9, said light guide 15 and said image guide 16 exit the second channel 14 in the central portion 6 of said main tube 2 and are connected to a first three ways connector 17 on three separated inputs.

Figure 4:
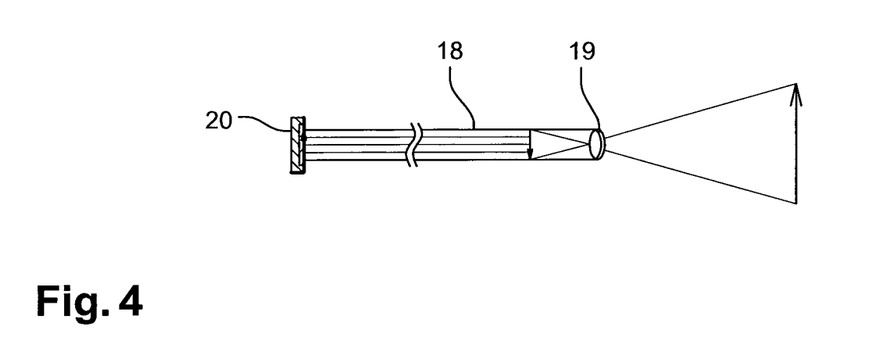
FIG. 4 is schematic representations of the image guide of the endotracheal intubation device according to the present invention.

The FIG. 4 represents three different alternatives to arrange the image guide 16. As shown on FIG. 4, the image guide 16 can include for example of a flexible fiber bundle image guide 18 provided with a lens 19 at its distal end. The lens 19 diameter is roughly equal to the image guide 16 diameter and is tightly integrated to it in order to form a smooth, continuous assembly incorporated into the peripheral wall 3. The focal length of the lens 19 and its positioning is chosen so as to create an image of objects in front of the distal end of the main tube 2 on the distal end surface of the flexible fiber bundle 18. In the first alternative shown on FIG. 4, the flexible fiber bundle 18 terminates directly into said first three ways connector 17 in a manner that it is adapted to be directly coupled with an image sensor 20 mounted into a control panel 100, 400 as described in FIG. 8, 9 or 10.

According to the second alternative shown on FIG. 4, the proximal end of said flexible fiber bundle image guide 18 can be provided with another lens 21 mounted in the same way the lens 19 is, said lens 21 being able to focalize an image on said image sensor 20.

The third alternative shown on FIG. 4 proposes to replace the lens 21 by a fused fiber bundle image guide 22 adapted to said image sensor 20.

Data from the image sensor 20, for example CMOS, are gathered and transformed into a video signal.

Figure 5:
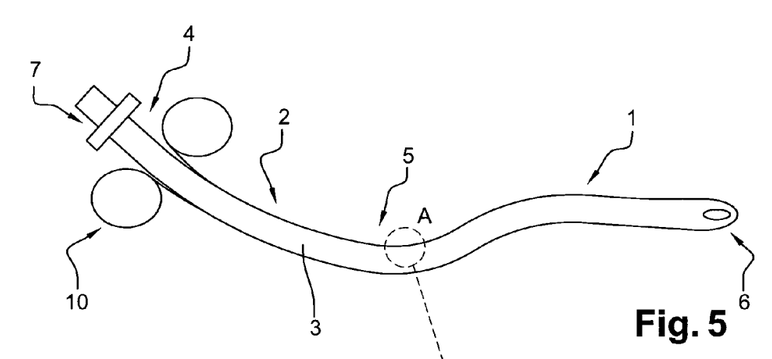
FIG. 5 is a schematic view of an endotracheal intubation device according to the present invention.

The FIG. 5 represents a schematic view of an andotracheal intubation device 1 represented on FIG. 1, whereas the detail A encircle a transversal groove 23 made in the peripheral wall 3 in order to bring flexibility to the main tube 2.

Figure 6:
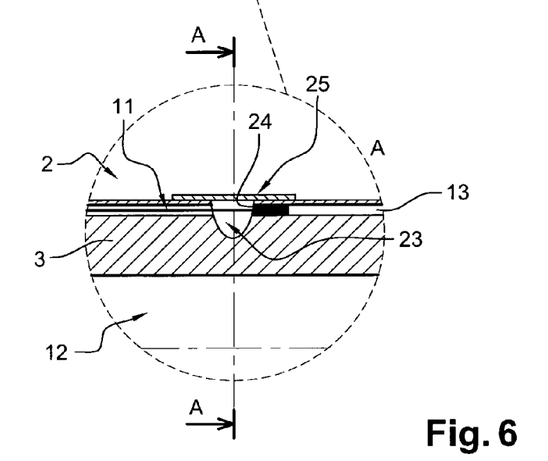
FIG. 6 is a large-scaled and longitudinal cross section view of the detail A of FIG. 5.

The FIG. 6 represents a large-scaled and longitudinal cross section view of the detail A of FIG. 5, showing a part of said peripheral wall 3 and a transversal groove 23. Said guiding channel 13 extends from the central portion to at least a transversal groove 23 and guides a pulling line 11. Said pulling line 11 straddles said transversal groove 23 and is blocked towards the proximal direction by locking means 24, for example an abutment, so that pulling said pulling line 11 in the proximal direction would bring the edges of said transversal groove 23 closer and bend the main tube 2. A thin flexible patch 25 can cover said transversal groove 23.

Figure 7:
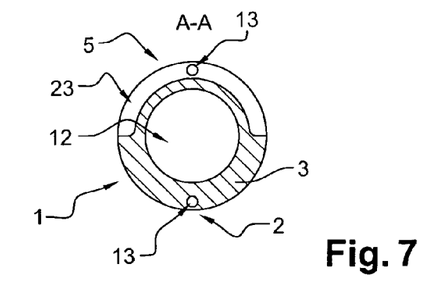
FIG. 7 is a transversal cross section of the endotracheal intubation device shown on FIG. 5 according to the axis A-A of the FIG. 6.

FIG. 7 represents a cross section according to the Axis A-A of the FIG. 6 and shows that a transversal groove 23 extends along about a half of the diameter of the main tube 2. Two transversal grooves 23 realized in an antagonistic manner at some distance from each other permit to the practitioner to obtain easily an "S"-shaped bending, when needed, using only two fingers of one hand.

Figure 8:
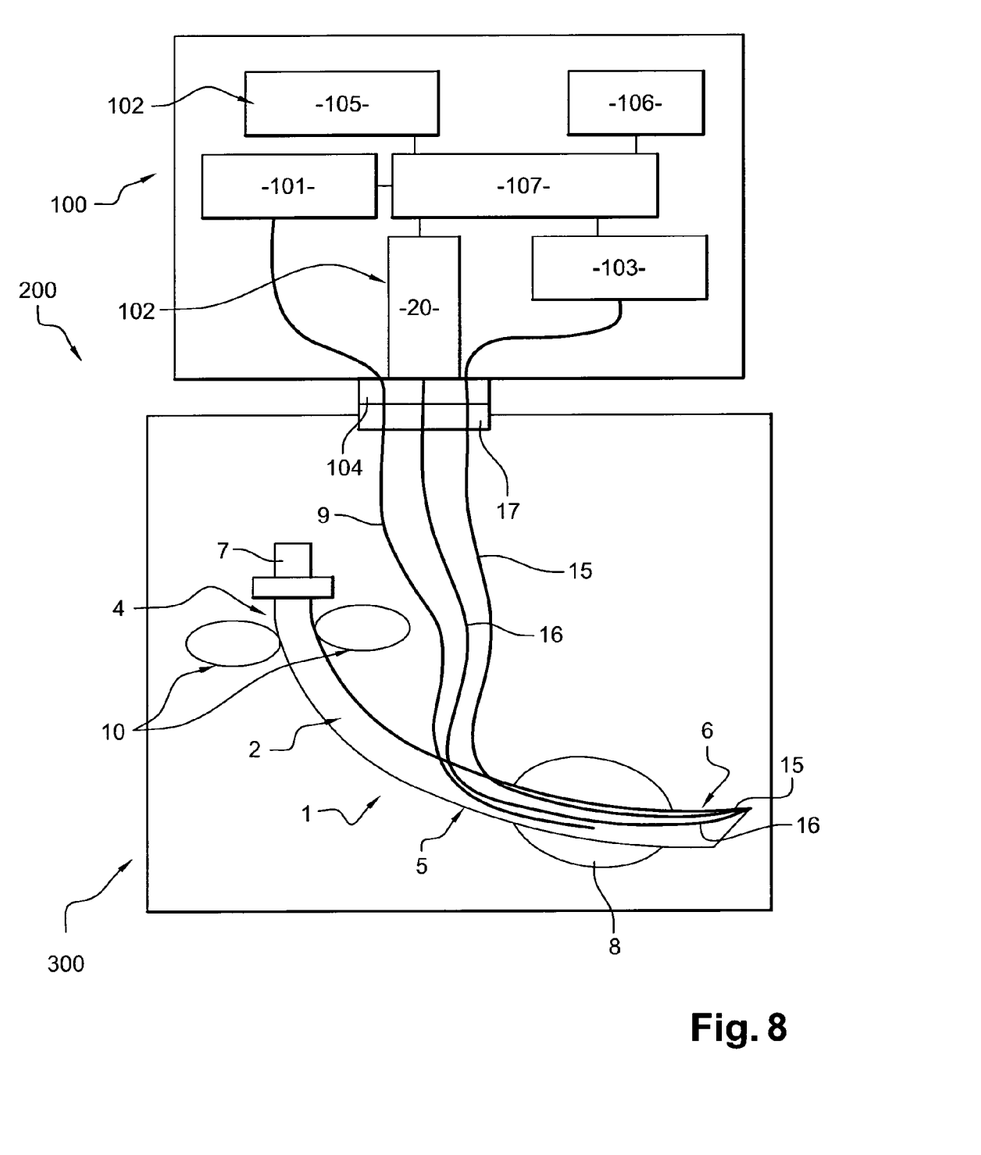
FIG. 8 is a schematic view of an endotracheal intubation assembly according to the invention.

The FIG. 8 represents a schematic view of an endotracheal intubation device 1 connected to a control panel 100 according to the present invention and included in an intubation assembly 200 of the present invention. The control panel 100 comprises a pressure regulator 101, image means 102, a light source 103 and a third three ways connector 104.

Said third three ways connector 104 is adapted to link said inflation tube 9 of the endotracheal intubation device 1 to said pressure regulator 101 through a first way so as to allows the pressure regulator 101 to control and adapt the pressure inside said cuff 8. For example, the pressure is regulated by use of a sterile compressed air cartridge device incorporated into the pressure regulator 101. In order to inflate the cuff 8 to the required pressure, said pressure regulator is preset to a value corresponding up to a column of water of 35 cm high. A correct intra-cuff pressure does not restrict tracheal tissue blood flow and reduces chance of tissue damage, even during long-term intubation. This first way incorporates, for example, the mechanical self-sealing valve of a Luer tip.

A second way of the third three ways connector 104 is dedicated to connect said light source 103 to light guide 15, thus transmitting light to the distal end of said endotracheal intubation device 1 delivering enough light for said image means 102 to work properly in either the presence or absence of the classical laryngoscope lighting, i.e before or after the endotracheal intubation device 1 penetrates the patient's trachea. The area around the distal end of the main tube 2 is enlighted by the light that exits the light guide 15 and feeds the image guide 16 with a view of said area. Typically, said image guide 16 comprises a fiber optics.

A third way of the third three ways connector 104 is dedicated to connect said image means 102 and the image guide 16. Said image means 102 are, for example, comprising an image sensor 20 and a display device 105. The image sensor 20 faces the proximal end of the image guide 16, thus bringing the image in front of the distal end of the endotracheal intubation device 1 to the sensing, controlling and displaying part of the visualization system incorporated in the control panel 100, i.e the image means 102. The size of the image sensor 20 is a little bigger than the diameter of the image guide 16 so a direct coupling can be done.

Said control panel 100 is preferably provided with an autonomous power supply 106 that powers an electronic control units 107 which drives said pressure regulator 101, said image means 102 and said light source 103. Thanks to the pressure regulator 101, the practitioner can set up the pressure inside said cuff 8 and make certain the pressure will not change all through the intubation.

An endotracheal intubation device 1 according to the present invention can be sealed into a thight packaging 300 that keep the sterility of said endotracheal intubation device 1. The first three ways connector 17 is placed across the packaging 300 for a proper connection to the control panel 100 without impairing the sterility of the endotracheal intubation device 1.

Optionally, inside the packaging 300, the cuff 8 can be inserted into a tube 301 having a diameter of the order of that of a trachea, said tube 301 being inserted onto the inflatable cuff 8 of said endotracheal intubation device 1. Said tube 301 permits to inflate the cuff 8 into the sealed packaging 300 and then to test its airtightness without opening said packaging 300 or impairing the sterility of the endotracheal intubation device 1. Preferably the tube 301 is provided with lubricant so that removing the endotracheal intubation device 1 from the packaging 300 lubricates the cuff 8.

Optionally, said packaging 300 comprises an identification tag, for example a radio frequency identification tag (RFID tag) or a bar code. The Identification tag contains for example a serial number or other information.

Inside the packaging 300, a test pattern 302 is placed so as to face the distal end of said endotracheal intubation device 1 placed therein. Said test pattern 302 allows to calibrate visualizing means 15, 16 of said endotracheal intubation device 1.

Figure 9:
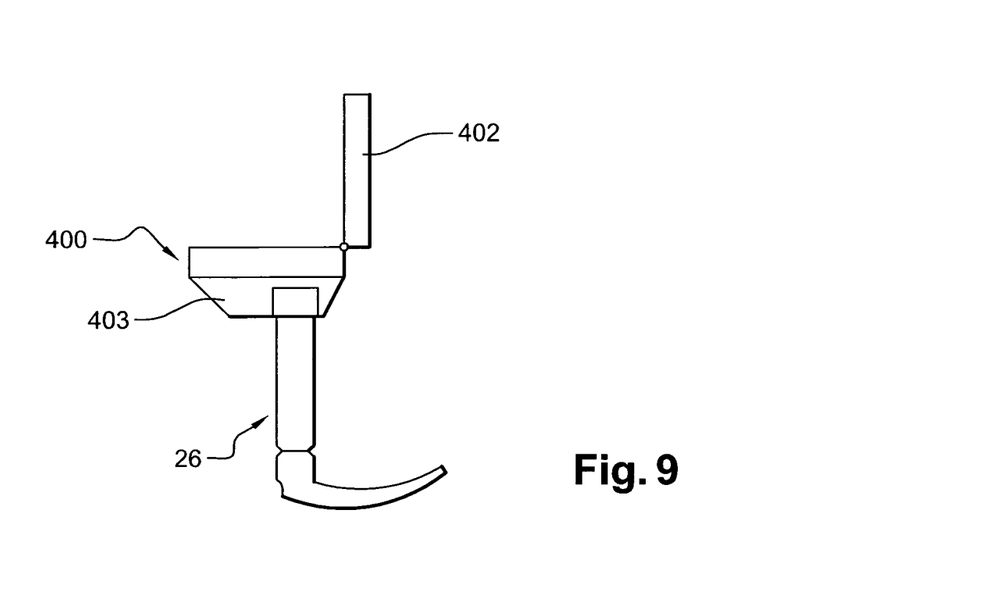
FIG. 9 is a side view of a control panel included in an intubation assembly according to the present invention mounted on a laryngoscope.
Figure 10:
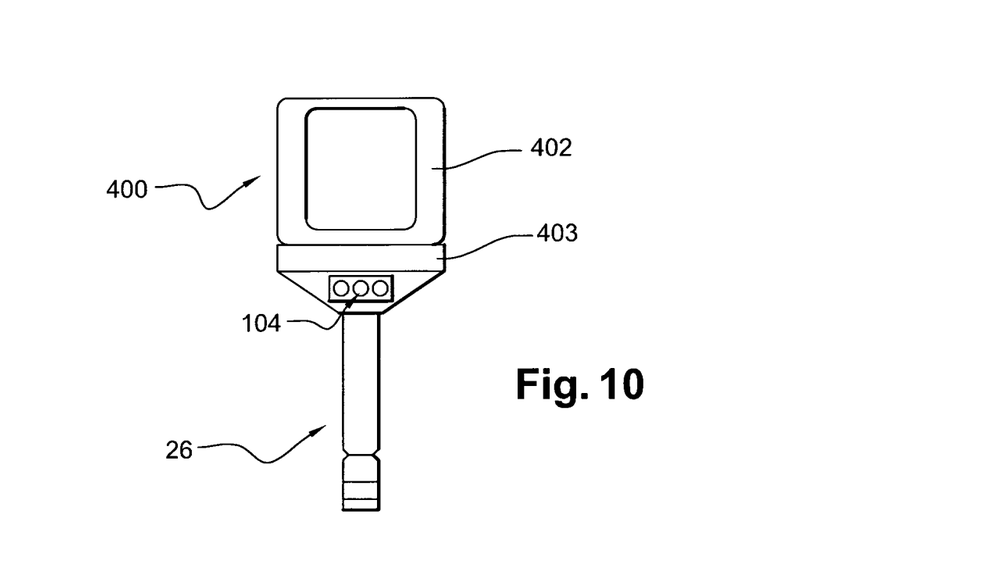
FIG. 10 is a front view of a control panel included in an intubation assembly according to the present invention mounted on a laryngoscope.

The FIGS. 9 and 10 shows a control panel 400 adapted to be mounted on a classical laryngoscope 26. The control panel comprises a bottom plate 403 wherein said thrid three ways connector 104 is mounted and which permits to connect the endotracheal intubation device 1. Said bottom plate 403 is also provided with a screen 402, optionally foldable, allowing to display the image of the trachea captured by the image guide 16 of said endotracheal intubation device 1 during intubation. The image of the patient's upper aerial ways can be seen on the screen 402 thus helping the practitioner penetrate into the patient's trachea. The image displayed on said screen 402 plays two important roles: help in guiding all through the penetration of the trachea and also supervising the trachea after the endotracheal intubation device 1 is installed. For this second function, a color video is preferred.

Figure 11:
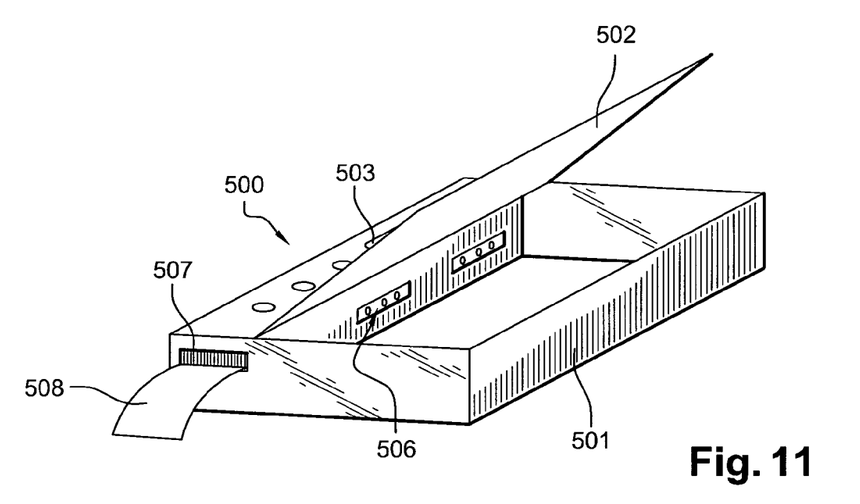
FIG. 11 is a perspective view of a endotracheal intubation device tester according to the present invention.
Figure 12:
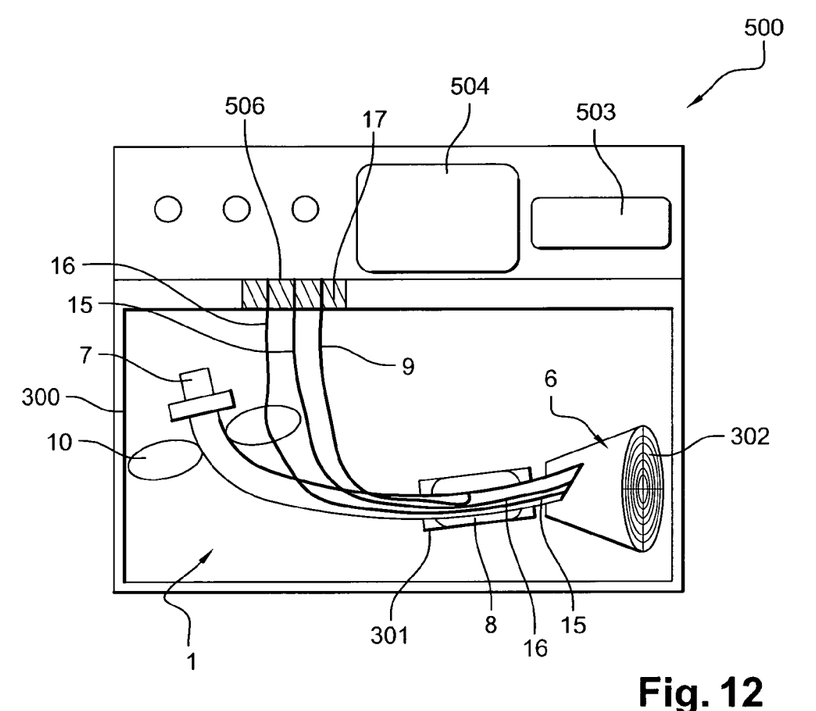
FIG. 12 is a bottom view of the endotreacheal intubation device tester of FIG. 11 containing a packaging according to the present invention.

The FIGS. 11 and 12 represent an endotracheal intubation device tester 500 according to the present invention. The endotracheal intubation device tester 500 comprises a case 501 adapted to receive a packaging 300 or an endotracheal intubation device 1, said case 501 being closed by a cover 502. The endotracheal intubation device tester 500 further comprises a pressure controller 503, an optical or video device 504, a test light source 505 and a second three way connector 506 as represented on FIG. 12. Said second three way connector 506 is connectable to said first three ways connector 17 of the endotracheal intubation device 1, said inflation tube 9 and said pressure controller 503 being connectable together through a first way of said first and second three ways connectors 17, 506, said test light source 505 and said means to enlighten 15 being connectable together through a second way of said first and second three ways connectors 17, 506, and said optical or video device 504 and said image guide 16 being connectable together through a third way of said first and second three ways connectors 17, 506. The optical or video device 504 are adapted to display the image captured by the image guide 16 of the endotracheal intubation device 1.

Once said first three ways connector 17 and said second three ways connector 504 linked, as shown on FIG. 12, the endotracheal intubation device tester 500 is able to test the vizualisation means 15, 16 and the inflatable cuff 8.

The light emitted by test light source 505 is transmitted to said means to enlighten 15 via the first and second three ways connector 17, 506 and this light light up the area around the distal end portion 6 of the endotracheal intubation device 1. The visualization means 15, 16 are tested with help of an adequate test pattern 302 placed inside the packaging 300 and facing the distal end of the endotracheal intubation device 1 so as to be lit by the light guide 15 and seen by the image guide 16. The image is then guided to the control panel 100 by the image guide 16 and seen by the testing person with the appropriate optical or video device 504 which can be for instance an eyepiece or a video system similar to that of the control panel 100.

The test of the inflatable cuff 8 is made thanks to the pressure controller 503 connected to the inflation tube 9 by blowing air to a controlled pressure. In order to keep the cuff 8 and its tube sterile the air used for testing must be sterile. Testing air is filtered before entering a reversible micro air pump not shown on Figures and designed to inflate and deflate the cuff 8. Alternatively, a sterile air cartridge can be used. The cuff 8 must be empty prior to the intubation.

Inside the packaging 300 the cuff 8 is enveloped with the non expandable tube 301 having an internal diameter similar to the patients trachea. When the cuff 8 is inflated its diameter is limited by the tube 301 and the pressure inside the cuff 8 is then set to a pressure corresponding to the weight of a column of water of about 25 cm high. If this pressure is achieved and kept for a preset time the cuff test is OK.

Once the test is accomplished, a printer 507 prints the results obtained on a sticker 508 and adds the date/time of test (FIG. 11). The packaging 300, with said sticker 508 stuck on it, is ready to be used for a given period of time. Since testing with the endotracheal intubation device tester 500 does not impair the sterility of the endotracheal intubation device 1, it can be brought to the operating theatre, kept if not used, and eventually re-tested later on. In all other known solutions an endotracheal intubation device entered to the operating theatre must be opened, tested, and, even if not used, finally disposed of at the end of the operation.

Optionally, the endotracheal intubation device tester 500 according to the present invention is provided with identification means to read for example a bar code or a radio frequency identification tag (RFID). The identification means are adapted to read the identification tags of the packaging 300.

The method of the present invention will now be detailed:

To practice the intubation method according to the present invention, it is recommended to dispose of the following material: a packaging according to the present invention, a control panel mountable on a laryngoscope as described above and an endotracheal intubation device tester according to the present invention. The preset pressure of the inflatable cuff should be preferably set to a pressure corresponding to a column of water of 35 cm high.

The packaging containing the endotracheal intubation device allows testing of visualization means and said inflatable cuff. Moreover, the endotracheal intubation device is lubricated while removed from its packaging.

- a modified laryngoscope or a classical larygoscope should be adapted with a control panel according to the present invention in order to present the following features:
- a pivoting screen (automatically switched on when opened) allowing the seeing of the image on the distal end of the endotracheal intubation device once connected to the control panel;
- sterile, disposable compressed air cartridge for the rapid cuff inflation;
- Inflation may be started with finger of the hand that holds the laryngoscope. Integrated connector for the transmission of images and compressed air for the cuff with automatic disconnection when the cuff pressure equals the preset value.

The endotracheal intubation device tester according to the present invention will provide the following advantages:

- allowing testing of vizualisation means of the endotracheal intubation device and testing of the cuff inflation while preserving the asepsis of the endotracheal intubation device;
- optical barcode reader for the tube serial number identification;
- a sticker printer to print data to be stick on the tube package without opening (and to be stuck on the anesthesia document after opening of the package);

To carry out the method according to the present invention, the following algorithm is to be followed:

I. Put a packaging containing a sterile endotracheal intubation device according to the present invention without opening the packaging into the endotracheal intubation device tester; close the cover of the endotracheal intubation device tester and starts the auto test:

- read the serial number of the endotracheal intubation device;
- test the vizualisation means;
- test the cuff pressure;
- print the results of the auto test on the sticker (and eventually store the data in the memory);

In case the test is not successfully passed, the packaging is disposed of.

In case the test is successfully passed, then step II.

II. At this step two cases are possible:

A) Intubation is not immediate open the tester cover and remove the tube package without opening it then place the sticker on the packaging (possibly replace the sticker onto the anesthesia document for intubation).

The packaging according to the invention can be tested and stored. At any step the sterility of the endotracheal intubation device is not impaired. In opposite, a classic endotracheal intubation device must be removed from its classic sterile packaging in order to be tested and can not thus be stored afterwards.

B) Intubation is immediate

1) Open the cover together and remove the endotracheal intubation device form its sterile packaging triggering the cuff lubrication;
2) Then place the sticker on the anesthesia document.
3) Then Connect the endotracheal intubation device to the control panel mounted on the laryngoscope with the help of the three ways connectors.
4) Then, depending on the visibility of vocal cords:
a) Vocal cords are well visible with the laryngoscope:

Direct (classic) intubation followed by the cuff inflation with sterile air from the cartridge (integrated to the laryngoscope) and automatic disconnection of the endotracheal intubation device when the pressure in the cuff equals the preset value.

Reconnect the introduced endotracheal intubation device to the endotracheal intubation device tester in order to check the position of the probe and verify or modify the cuff pressure.

b) Impossible to see vocal cords with the laryngoscope:

open the display of the control panel (automatic switch on);

guide the endotracheal intubation device using the image from the distal end transmitted with the vizualisation means and using the guiding means;

inflate the cuff with sterile air from the cartridge (integrated to the laryngoscope) and automatic disconnection of the endotracheal intubation device when the pressure in the cuff equals the preset value;

Reconnect the introduced endotracheal intubation device to the endotracheal intubation device tester in order to check the position of the probe and verify or modify the cuff pressure.

The above intubation method permits in particular to keep the sterility of the endotracheal intubation device while testing it.

During an operation, an endotracheal intubation device must be available and must have been tested. A classic endotracheal intubation device is removed from its sterile packaging and tested prior to any surgical intervention. At the end of the surgical intervention, no matter the endotracheal intubation device has been used, it must be disposed of.

Though the endotracheal intubation device and the packaging according to the present invention are more elaborated than a classic endotracheal intubation device, their use is cost-effective as the packaging does not need to be open prior to the surgical intervention and can be re-used after the surgical intervention. The guiding means and the visualization means of said endotracheal intubation device ensure a safer intubation even in case of difficult intubation.

The present application provides an endotracheal intubation assembly, an endotracheal intubation tester, a packaging and a method that resolve most if not all the issues occurring during an intubation.

The invention claimed is:

1. An endotracheal intubation device comprising:
   a main tube having a peripheral wall,
   a proximal end portion,
   a central portion,
   a distal end portion, and
   an inflatable cuff being disposed on the main tube in sealed relation thereto adjacent to the distal end portion and connected to an inflation tube and visualization means,
   wherein said visualization means comprise means to enlighten the area around the distal end portion towards an intubation direction, and wherein an image guide extends from the distal end portion to at least the proximal end portion,
   wherein said means to enlighten, said image guide, and said inflation tube are associated to a first three ways connector adapted to connect said endotracheal intubation device to a control panel.

2. The endotracheal intubation device including according to claim 1 further comprising controlling means for directing the distal end portion, wherein controlling means comprise proximal prehension means linked to bending means, said bending means being integrally mounted in the peripheral wall in the central portion of said main tube in a way to permit bending of the main tube.

3. The endotracheal intubation device according to claim 2, wherein said bending means comprise at least one transversal groove made on said peripheral wall and a plurality of pulling lines, each pulling line being adapted to bring edges of the transversal groove closer.

4. The endotracheal intubation device according to claim 3, wherein said prehension means comprise two manipulation rings.

5. The endotracheal intubation device according to claim 3, wherein a plurality of transversal grooves are realized at some distance from each other.

6. The endotracheal intubation device according to claim 3, wherein each said pulling line slides inside a longitudinal channel incorporated into the peripheral wall and extends to at least the distal edge of a transversal groove, and wherein the distal end of the pulling line is blocked towards a proximal direction by locking means so that said pulling line constantly straddles said transversal groove.

7. A packaging containing an endotracheal intubation device according to claim 1, wherein said packaging is adapted to seal and maintain said endotracheal intubation device in sterile conditions and wherein said first three ways connector extends outside said packaging.

8. The packaging according to claim 7, further comprising a tube having a non expandable diameter of a trachea, said tube being inserted onto the cuff of said endotracheal intubation device.

9. The packaging according to claim 7, further comprising a test pattern placed inside said packaging so as to face the distal end of said endotracheal intubation device placed therein, said test pattern allowing to calibrate visualizing means of said endotracheal intubation device.

10. An endotracheal intubation device tester comprising a case adapted to receive the packaging according to claim 7, a cover to close said case, a pressure controller, an optical or video device, a test light source and a second three way connector connectable to said first three ways connector of the endotracheal intubation device, said inflation tube and said pressure controller being connectable together through a first way of said first and second three ways connectors, said test light source and said means to enlighten being connectable together through a second way of said first and second three ways connectors, and said optical or video device and said image guide being connectable together through a third way of said first and second three ways connectors.

11. An intubation assembly comprising the packaging according to claim 7 and a control panel wherein said control panel comprises a pressure regulator, imaging means, a light source, and a third three ways connector, said inflation tube and said pressure regulator being connectable together through a first way of said first and third three ways connectors, said light source and said means to enlighten being connectable together through a second way of said first and third three ways connectors, said image guide and said imaging means being connectable together through a third way of said first and third three ways connectors.

12. An intubation method using the intubation assembly according to claim 11 and comprising a preliminary step of testing said endotracheal intubation device with the help of an endotracheal intubation device tester without impairing the sterility of said packaging.

13. The intubation assembly according to claim 11, wherein said imaging means comprise an image sensor adapted to transmit a video signal to a display device.

14. The intubation assembly according to claim 11, wherein at least said imaging means are mounted on a laryngoscope.

15. The intubation assembly according to claim 11, further comprising an endotracheal intubation device tester including a cover to close said case, a pressure controller, an optical or video device, a test light source and a second three way connector connectable to said first three ways connector of the endotracheal intubation device, said inflation tube and said pressure controller being connectable together through a first way of said first and second three ways connectors, said test light source and said means to enlighten being connectable together through a second way of said first and second three ways connectors, and said optical or video device and said image guide being connectable together through a third way of said first and second three ways connectors.

16. An intubation assembly comprising the endotracheal intubation device according to claim 1 and a control panel wherein said control panel comprises a pressure regulator, imaging means, a light source, and a third three ways connector, said inflation tube and said pressure regulator being connectable together through a first way of said first and third three ways connectors, said light source and said means to enlighten being connectable together through a second way of said first and third three ways connectors, said image guide and said imaging means being connectable together through a third way of said first and third three ways connectors.

17. The intubation assembly according to claim 16, wherein said imaging means comprise an image sensor adapted to transmit a video signal to a display device.

18. The intubation assembly according to claim 16, wherein at least said imaging means are mounted on a laryngoscope.

19. The intubation assembly according to claim 16 comprising a case wherein said packaging is adapted to seal and maintain said endotracheal intubation device in sterile conditions and wherein said first three ways connector extends outside said packaging and further comprising an endotracheal intubation device tester including a cover to close said case, a pressure controller, an optical or video device, a test light source and a second three way connector connectable to said first three ways connector of the endotracheal intubation device, said inflation tube and said pressure controller being connectable together through a first way of said first and second three ways connectors, said test light source and said means to enlighten being connectable together through a second way of said first and second three ways connectors, and said optical or video device and said image guide being connectable together through a third way of said first and second three ways connectors.

* * * * *